(12) United States Patent
Seal et al.

(10) Patent No.: US 6,333,988 B1
(45) Date of Patent: Dec. 25, 2001

(54) PERSONAL IDENTIFICATION

(75) Inventors: Christopher Henry Seal, Woodbridge; Maurice Merrick Gifford, Kesgrave; David John McCartney, Ipswich, all of (GB)

(73) Assignee: British Telecommunications PLC, London (GB)

( * ) Notice: Subject to any disclaimer, the term of this patent is extended or adjusted under 35 U.S.C. 154(b) by 0 days.

(21) Appl. No.: 09/194,737

(22) PCT Filed: Jun. 6, 1997

(86) PCT No.: PCT/GB97/01525
§ 371 Date: Dec. 2, 1998
§ 102(e) Date: Dec. 2, 1998

(87) PCT Pub. No.: WO97/46979
PCT Pub. Date: Dec. 11, 1997

(30) Foreign Application Priority Data

| Jun. 6, 1996 | (GB) | 9611787 |
| Oct. 18, 1996 | (GB) | 9621900 |
| Sep. 18, 1997 | (EP) | 97302580 |

(51) Int. Cl.[7] .................. G06K 9/24; A61B 3/14
(52) U.S. Cl. .......... 382/117; 382/313; 396/18; 351/206; 351/210; 351/221
(58) Field of Search .................. 359/600, 611, 359/894; 396/18; 356/71; 348/78; 713/186; 382/117, 313; 340/5.52, 5.82; 351/206, 207, 210, 211, 221; 902/3, 6, 5

(56) References Cited

U.S. PATENT DOCUMENTS

| 4,109,237 | 8/1978 | Hill | 340/146.3 E |
| 4,256,384 | 3/1981 | Kani et al. | 351/7 |
| 4,266,861 | 5/1981 | Sawa | 351/7 |
| 4,304,468 | * 12/1981 | Wada | 351/13 |
| 4,394,074 | 7/1983 | McMahon et al. | 351/206 |

(List continued on next page.)

FOREIGN PATENT DOCUMENTS

| 30 40 009 A1 | 5/1981 | (DE) | A61B/3/10 |
| 0061832 A2 | 10/1982 | (EP) | A61B/5/10 |
| 0 126 549 A2 | 11/1984 | (EP) | A61B/3/14 |
| 0534477 A1 | 9/1992 | (EP) | G03B/17/53 |
| 2461481A1 | 2/1981 | (FR) | A61B/3/14 |

(List continued on next page.)

OTHER PUBLICATIONS

Karla Harby, "A Discerning Eye", p. 29, Scientific American, Apr. 1996.

Anjana Ahuja, "A Peep into the Future of Iris ID", The Times, Apr. 14, 1996.

Japanese Giant Spends US $25.8M on Iris Scanning Technology, Biometric Technology Today, vol. 3, No. 6, Oct. 1995.

(List continued on next page.)

Primary Examiner—Matthew C. Bella
Assistant Examiner—Brian P. Werner
(74) Attorney, Agent, or Firm—Nixon & Vanderhye. P.C.

(57) ABSTRACT

A personal identification apparatus for providing information characteristic of an eye includes a housing with an entrance window through which a user looks at a target object. An image capture device within the housing operates to provide an image signed representing features of the eye and responsive to non-visible light reflected from the eye. In addition to the illumination source for the non-visible light reflected from the eye the apparatus also includes an optical element substantially transparent to the non-visible light and which has a first region less transparent to visible light from the target object than a second region. The arrangement of the apparatus is such that the image capture device views the eye through the second region of the optical element and the eye views the target object through the first region of the optical element.

15 Claims, 5 Drawing Sheets

U.S. PATENT DOCUMENTS

| | | | |
|---|---|---|---|
| 4,533,222 | 8/1985 | Ishikawa | 351/206 |
| 4,620,318 | 10/1986 | Hill | 382/2 |
| 4,641,349 | 2/1987 | Flom et al. | 382/2 |
| 4,755,043 | 7/1988 | Carter | 351/205 |
| 4,786,142 | 11/1988 | Karecki | 350/319 |
| 4,821,118 | 4/1989 | Lafreniere | 358/225 |
| 4,834,528 | 5/1989 | Howland et al. | 351/211 |
| 4,993,068 | 2/1991 | Piosenka et al. | 380/23 |
| 5,118,179 | 6/1992 | Sano et al. | 351/206 |
| 5,214,454 | 5/1993 | Sano | 351/206 |
| 5,291,560 | 3/1994 | Daugman | 354/62 |
| 5,359,669 | 10/1994 | Shanley et al. | 382/6 |
| 5,433,197 | 7/1995 | Stark | 128/633 |
| 5,485,241 | 1/1996 | Irie et al. | 354/410 |
| 5,572,596 | 11/1996 | Wildes et al. | 382/117 |
| 5,576,780 * | 11/1996 | Yancey | 351/211 |
| 5,576,796 | 11/1996 | Akashi | 396/51 |
| 5,684,562 * | 11/1997 | Fujieda | 351/212 |

FOREIGN PATENT DOCUMENTS

| | | | |
|---|---|---|---|
| 2516778A1 | 5/1983 | (FR) | A61B/3/10 |
| 2521851A1 | 8/1983 | (FR) | A61B/3/12 |
| 2604080A1 | 9/1986 | (FR) | A61B/3/12 |
| 2627074A1 | 2/1988 | (FR) | A61B/3/10 |
| 2630365A1 | 4/1988 | (FR) | B23P/19/04 |
| 2690329A1 | 4/1992 | (FR) | A61B/3/113 |
| 2119941A | 11/1983 | (GB) | G03B/13/02 |
| 2201801A | 9/1988 | (GB) | G03B/17/48 |
| WO 86 05018A1 | 8/1986 | (WO) | G06K/9/00 |
| WO 89/04139A1 | 5/1989 | (WO) | A61B/3/12 |
| WO 92 05736 A1 | 4/1992 | (WO) | A61B/3/02 |
| WO 92/05736A1 | 4/1992 | (WO) | A61B/3/02 |
| WO 94/09446A1 | 4/1994 | (WO) | G06K/9/00 |
| WO 94/10900A1 | 5/1994 | (WO) | A61B/3/14 |
| WO 96/07978A1 | 3/1996 | (WO) | G06K/9/00 |
| WO 97/05578A1 | 2/1997 | (WO) | G07C/9/00 |

OTHER PUBLICATIONS

Cope, The Corneal Polarisation Cross, J. Opt. Soc. of America, vol. 68, No. 8, pp 1139–1140, 1978.

Robbins, Biological Perspectives on Human Pigmentation, pp. 74–75, 1991.

Radke, Auf einem Blick, Funkschau, vol. 59, No. 1, Jan. 1987, Munchen.

Industrial Cryptography, IEE Review, May 1996—sales brochure.

Daugman, "High Confidence Visual Recognition of Persons by a Test of Statistical Independence", IEEE Transactions of Pattern Analysis and Machine Intelligence, vol. 15, No. 11, Nov. 1993.

Collection of web–pages from Identification Technologies International, 1997.

Web–page describing Sensar Inc.'s "I risident" system, 1997.

Radke: "Auf einen Blick" Funkschau vol. 59, No. 1, Jan. 1987, Munchen DE, pp. 34–36, XP002022145 see the whole document.

* cited by examiner

PERSONAL IDENTIFICATION

RELATED APPLICATIONS

This application is related to the following co-pending commonly assigned applications:
1. Seal et, "Personal Identification", Ser. No. 09/194,319 filed Nov. 24, 1998.
2. Seal et al, "Personal Identification", Ser. No. 09/194,318 filed Nov. 24, 1998.
3. McCartney et al, "Imaging Apparatus", Ser. No. 09/180,760 filed Nov. 13, 1998.

This application is the national phase of international application PCT/GB97/01525 filed Jun. 6, 1997 which designated the U.S.

BACKGROUND OF THE INVENTION

1. Field of the Invention

The present invention relates to personal identification and apparatus, methods and uses therefor.

2. Related Art

In today's world of electronic communication and commerce, the ability to identify a person, for the purposes of security in remote transactions is paramount. A common form of security is a simple password which, for example, is entered when a user wishes to access a computer network. Another form of security, which is widely used in bank automatic teller machines (ATMs), is a personal identification card, which holds on a magnetic strip encoded information such as the owner's personal details and account number, which is used in combination with a personal identification number (PIN) entered by the user when the transaction is initiated.

Various ways have been demonstrated of fraudulently by-passing the above-described and other commonly used security measures to gain access to private information or resources. Such security problems are discussed in the article entitled "Industrial Cryptography" in the IEE Review dated May 1996. As the title suggests, this article focuses on how cryptography can be used effectively as a way of increasing security.

Another way of ensuring the identity of a user is to capture and encode a biometric from the party and compare the result with a previously-stored, or enrolled, result, for example stored on a remote database system. A biometric, for the present purposes, is a statistical or quantitative measure of a biological feature of a person. The most well-known biometric for humans, used for identification purposes, is the fingerprint. A 'robust' biometric, such as a fingerprint, is one which can be used reliably and repeatedly to identify a person.

Recently, the use of the iris of an eye as a robust biometric for identification purposes has been proposed. U.S. Pat. No. 5,291,560, dated Mar. 1, 1994, describes a method of encoding the image of an iris into a 256-byte iris code. It has been shown that such a code can be used as a very reliable personal identifier.

One proposed example of the use of an iris code is for identifying a customer attempting to withdraw cash from an ATM (automatic teller machine). The proposed ATM includes an imaging system which comprises a window through which the customer looks and an auto-focusing camera. The camera is positioned directly in the line of sight of the customer. When the customer looks through the window and, for example, inserts his bank card into the ATM, the camera captures an image of his eye.

Once the system has captured a suitable representation of an eye, the representation is digitised (if not already in digital form) and encoded to form an iris code. This iris code can then be compared with a stored iris code of allegedly the same person. If the two codes are sufficiently similar, the identity of the customer is verified and cash withdrawal, for example, is permitted.

This system is designed to be non-intrusive and can be used by anyone wishing to withdraw money from the ATM.

Another apparatus which identifies/verifies a user by imaging the eye is disclosed in U.S. Pat. No. 5,369,669. This patent discloses a mobile retinal scan identifier.

Both the known apparatuses suffer from a drawback in that it is difficult for the user to align his eye with the apparatus accurately. If the user's eye is not accurately aligned then the apparatus may be unable to identify the user.

In accordance with the present invention there is provided an apparatus for providing an information signal characteristic of an eyes, said apparatus comprising:
    a housing having an entrance window;
    an image capture device mounted within the housing, in optical communication with said entrance window, and operable to provide an image signal representing one or more features of the eye responsive to non-visible light reflected from the eye;
    an illumination source operable to illuminate the eye with light, at least a portion of which is non-visible.

SUMMARY OF THE INVENTION

In accordance with the present invention there is provided an apparatus for providing an information signal characteristic of an eye, said apparatus comprising:
    a housing having an entrance window;
    an image capture device mounted within the housing, in optical communication with said entrance window, and operable to provide an image signal representing one or more features of the eye responsive to non-visible light reflected from the eye;
    an illumination source operable to illuminate the eye with light at least a portion of which is non-visible;
    a target object visible, in use, through said entrance window by the eye;
    an optical element interposed, in use, between said target object and the eye, said optical element being substantially transparent to said non-visible light, and having a first region which is less transparent to visible light from said target object than a second region.

In using an apparatus according to the present invention, a user is encouraged to look through (i.e. align his pupil with) the second region so that he obtains a clearer view of the target object. The image capture apparatus 'looks' through both regions of the optical element. By suitable arrangement of the first and second regions the field of view of the image capture apparatus relative to the pupil can be determined.

The apparatus may be adapted to be brought by the user to his own eye. Alternatively, the apparatus may be fixed, requiring the person whose eye is being investigated to align his head accordingly.

Preferably, the first region is surrounded by the second region this enables an image of the eye around the pupil to be captured. If the first region is substantially at the centre of the second region then, advantageoulsy, an image centreed around the pupil of the user is obtained. In embodiments of the invention, correct eye alignment may be achieved by providing a window having a major region which is relatively less transmissive to visible optical radiation than a minor region of the window. The minor region would preferably be situated near or at the centre of the window and would be sufficiently small to require the pupil of an eye to be positioned close to the window, in alignment with the minor region, to see a reasonable field of view of, for example, the target equipment through the apparatus. Then, in use, the person looking through the window would be encouraged to align the pupil of their eye with the minor region of the window thereby ensuring that the iris of the eye would be substantially centrally positioned and thus correctly aligned with respect to the window for the purposes of information capture. Also, to some extent, appropriate sizing of the minor region would control the distance the user places his eye from the screen. This would be beneficial in terms of reducing or removing any need to focus the imaging means.

The minor region of the window may comprise a material having a different optical composition from the major region. The different composition would typically appear substantially transparent to visible wavelengths of optical radiation and comprise, for example, clear glass or plastics material. Alternatively, the minor region may simply be a hole appropriately positioned in the window material of the major region. The major region might comprise, for example, a gelatin filter which is transparent to IR and NIR radiation.

Preferably, when using non-visible wavelengths of optical radiation, for example IR or NIR radiation, for the purposes of eye illumination and image capture, the window is substantially uniformly transparent over the window area to those wavelengths. Thus, while the window has only a minor region suitable for viewing, and thus aligning, purposes, the whole area of the window can be used for image capture purposes.

In preferred embodiments, the target object comprises a second window which provides a "line-of-sight" for the user, through the first window, to allow the user to view the environment beyond the apparatus. The second window may be a simple opening in the housing or might possibly include a visual display.

Having a second window is particularly advantageous when combined with a cordless arrangement, since the user is able to see accurately where the apparatus is pointing whilst looking into the apparatus for the purpose of eye image capture: the user can direct the apparatus appropriately at the remote apparatus receiver. It is believed also that allowing the user to fixate on the remote equipment causes the pupil of the eye to contract thus providing a larger and clearer view of the iris. Also, to a large extent, the view through the second window can provide a means for aligning the eye correctly in relation to the imaging means. However, further means to aid alignment, for example cross-hairs, may be provided.

The second window may be employed to allow a user to view a remote screen on which one or more captured images of the eye are displayed. The benefit to the user in this case is that he can see on the screen substantially what the imaging means is seeing, and adjust his eye position for correct alignment if necessary. In this case the imaging means might be a video camera which is capable of transmitting real time images of the eye to the screen.

The apparatus preferably comprises an encoding means for encoding captured information prior to its transmission. This has the advantage that the signal transmitted from the apparatus requires less bandwidth (assuming the transmission is to be achieved in a given time) than would be required by the transmission of the image signal.

The encoding means is preferably arranged to encode at least the iris portion, or part thereof, of a captured image. The encoding means may also encode one or more further features of the eye or surrounding face. For example, the code might include details of the pupil, the cornea, the sciera, and/or the eyelids, etc.

Preferably, the apparatus is arranged to be carried into an operative position by a user; the illumination source is operable to illuminate the surface of the eye over an area outside the pupil; the image signal represents one or more features of the anterior of the eye; and the apparatus further comprises a transmission device operable to transmit said information signal derived from said image signal to a remote apparatus.

Such an apparatus is to be preferred to a retinal scanning apparatus since it requires a camera rather than complex and bulky scanning optics. The apparatus is therefore more easily brought to the eye as well as providing a more rapid alignment than hitherto possible.

The transmission device may comprise a cordless transmission device. This arrangement has the advantage that the user does not need to concern himself with physical cable connections, for example on the back of a PC. Also, a user is not so restricted in his position relative to the PC, or other remote equipment, during use of the apparatus. Various types of cordless link, for example an ultrasonic, optical or RF link might be used.

Preferably, the apparatus further comprises a wavelength selective reflector effective to reflect substantially all of either said visible light or said non-visible light and to allow the passage of substantially all of the other.

The advantage of this arrangement is that a high proportion of non-visible light reflected from the eye is directed towards the camera, thereby a better image to be obtained for a given level of illumination. The presence of the reflector also increases the depth of focus of the apparatus.

In preferred embodiments, the imaging apparatus further comprises means to encrypt an encoded image.

Encryption increases the security of the transmission from the apparatus. The encrypted image code data typically includes other encrypted data such as date, time, apparatus serial number and/or even a GPS (global positioning system) co-ordinate record. Such extra information, when held in encrypted form, further increases the security of the system. For example, an encrypted code including encrypted time and date information could be intercepted by an eavesdropper but could not easily be used again since the date and time combination would be unique.

The apparatus may further comprise receiver means to enable bi-directional communications with the remote apparatus. Preferably then optical communications can be utilised using, for example, infra-red transmitters and receivers (e.g photo-diodes). Such a 'cordless' arrangement might be used with remote apparatus having a suitable optical transmitter and receiver arrangement.

The illumination means preferably provides predominantly near-infra-red (NIR) or infra-red (IR) optical radiation. A substantially non-visible illumination source is believed to be more comfortable to the person whose eye is being investigated. Also, in a line-of-sight embodiment, a substantially non-visible illumination source detracts the user's attention less from the line-of-sight image of the surroundings than would a source of visible optical radiation. For convenience only, the term "light" is intended in this description to include non-visible wavelengths of optical radiation. For this reason, the terms "light" and "optical radiation" are interchangeable.

The apparatus preferably includes a trigger means. The trigger means may be operable by the user, by the apparatus itself or even, in a bi-directional embodiment, by the remote apparatus. Such arrangements allow the user, or one of the said apparatuses, to control exactly when image capture and/or when data transfer occurs. This feature finds particular application when using a cordless arrangement.

As well as being used to identify humans, the present apparatus can be used, in an appropriate form, to identify animals. Such an apparatus would typically need to be larger (depending on the size of the animal's eyes) and more robust. Suitable candidates for such a use are, for example, horses, and in particular expensive race-horses.

BRIEF DESCRIPTION OF THE DRAWINGS

Embodiments of the present invention will now be described, by way of example only, with reference to the following drawings, of which.

DETAILED DESCRIPTION OF EXEMPLARY EMBODIMENTS

Figure 1:
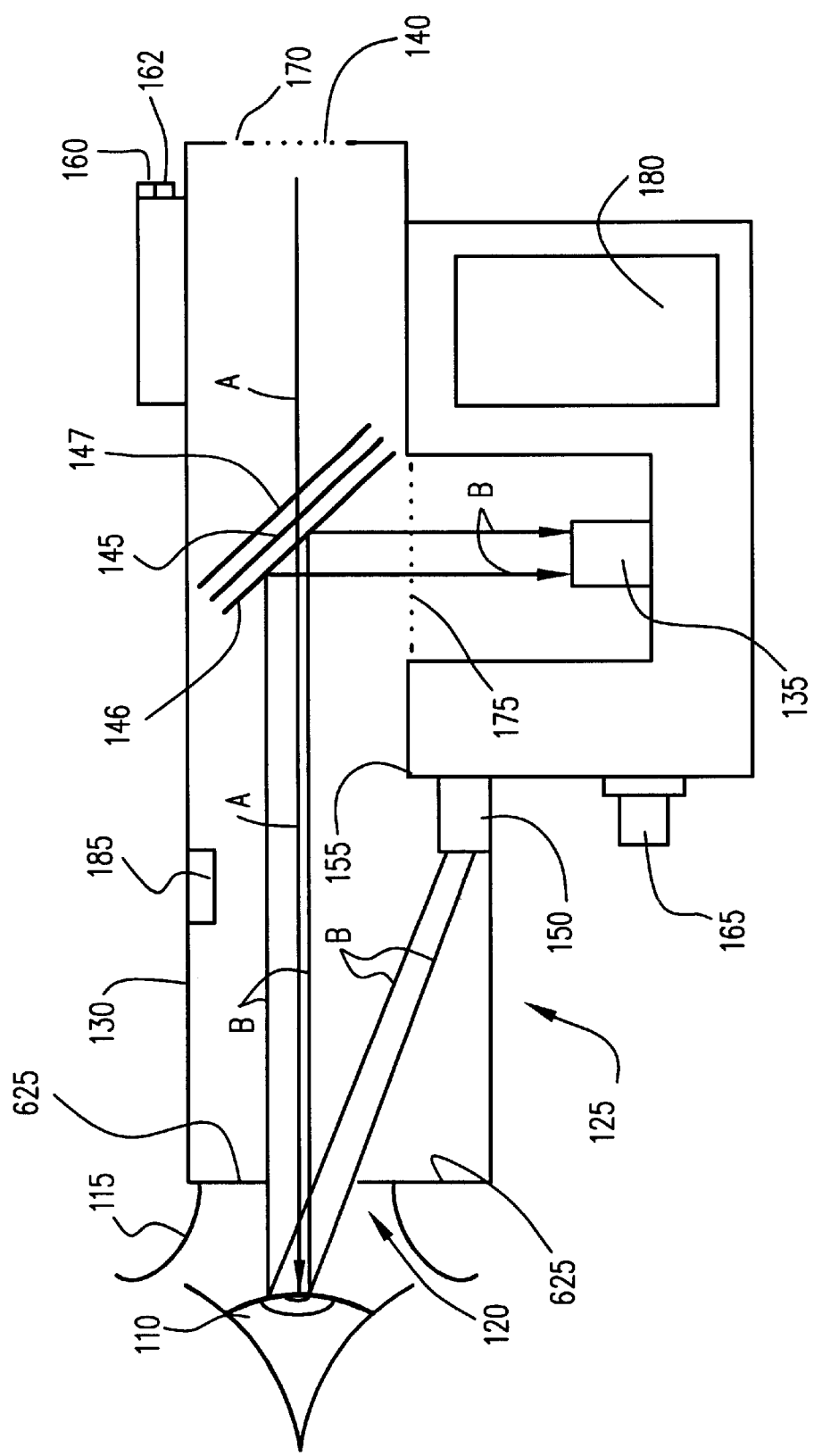
FIG. 1 is a schematic representation of an imaging apparatus.

FIG. 1 illustrates the imaging apparatus in use. The imaging apparatus is principally intended to be used by a single user and is thus designed to be intrusive, requiring a user to place his eye (and surrounding face) directly in contact with the apparatus. In the event it is intended that more than one user will use the apparatus, personal, replaceable eye-cups can be provided.

The apparatus is contained in a suitable housing 125. A user positions his eye 110 by placing his face appropriately against an eye-cup 115 at a rear window 120 of the housing 125. The rear window 120 of the apparatus may incorporate a screen 625. The eye-cup acts both as a means of minimising the amount of ambient light entering the apparatus and as the means for aligning the user's eye with the window.

The eye-cup 115 is attached to a barrel 130 formed in the housing 125 which provides a fixed separation between the eye 110 and a fixed-focus Charge Coupled Device (CCD) camera 135. The length, however, of the barrel 130 is adjustable to suit different users and is lockable once the correct length has been determined. The barrel 130 also provides a line-of-sight for the user, from the rear window 120 to a front window 140, through the housing 125. The adjustable barrel and fixed focus camera arrangement may be replaced by an auto-focusing camera arrangement. However, such an arrangement would increase the optical, electronic and mechanical apparatus complexity The optical path between the eye 110 and the camera 135 subtends an angle of 90° due to a partially reflecting, 45° mirror 145 in the line-of-sight of the barrel 130.

An infra-red (IR) illumination source 150 is located between the mirror 145 and the eye 110 to illuminate the eye. The source has an associated screen 155 to prevent light travelling directly from the source 150, via the mirror 145, to the camera 135.

An IR transmitter 160 and receiver 162 are located on the front of the housing 125, in line with the line-of-sight of the barrel 130, and a trigger button 165 is included on the housing for the user to control when the image is captured and/or transmitted to a remote apparatus (not shown).

As has already been mentioned, the connection between the apparatus and the remote apparatus might instead comprise a telephone line or similar connection, and the apparatus might then employ known modem technology to facilitate data transfer across the telephone line to and from the remote apparatus.

The front of the barrel 130 includes an IR filter 170 to minimise the amount of stray IR radiation that enters the apparatus. Additionally, the filter 170 might be useful to protect the user's eye from the accidental reflection of radiation emitted from the output of the transmitter 160. The CCD camera 135 is protected from stray visible light with a visible light filter 175 positioned between the camera and the barrel. The CCD camera is a standard black and white camera which is also sensitive to IR optical radiation. Other types of camera, for example a colour camera, could equally be used for image capture.

Figure 2:
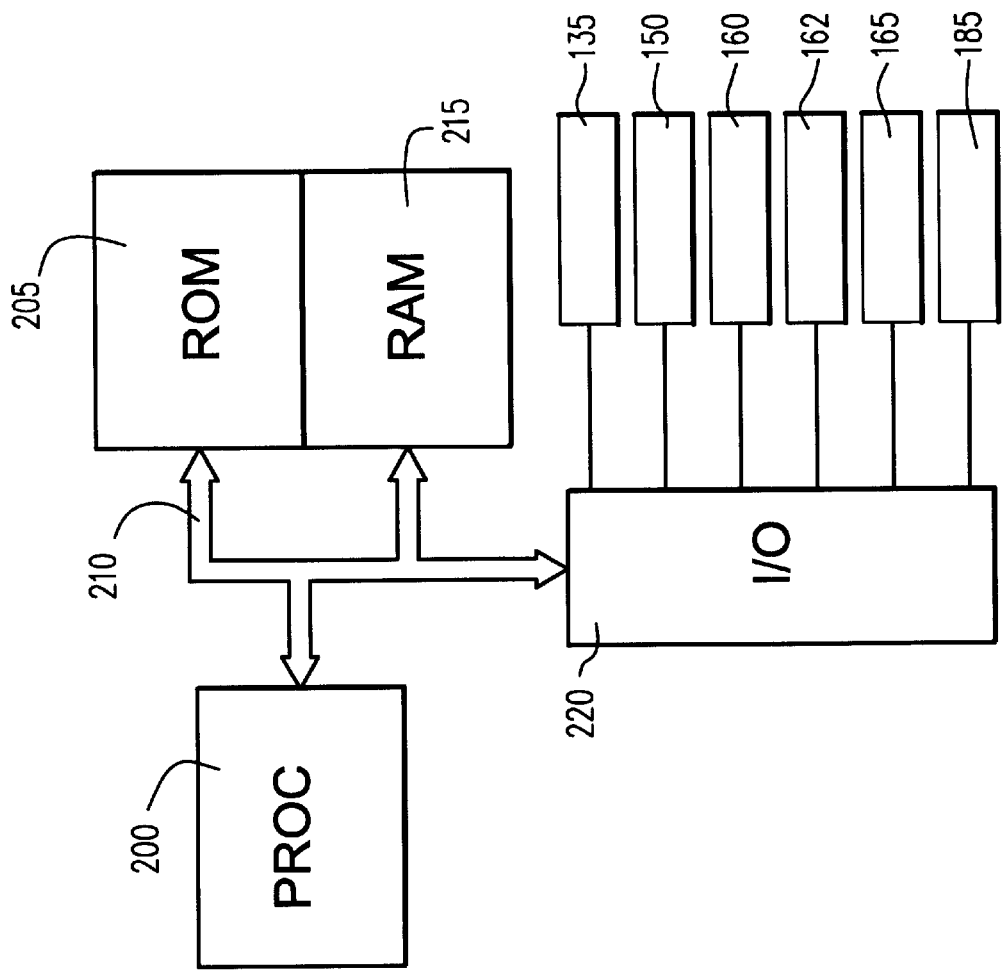
FIG. 2 is a schematic diagram which illustrates one possible hardware architecture for the imaging apparatus.

The apparatus also includes appropriate electronic circuitry 180 contained in the housing (described in more detail in relation to FIG. 2.).

An optical indicator 185 is positioned in the barrel, in the field of view of the user. The indicator comprises one or more LEDs of varying colours which can be illuminated to indicate different apparatus statuses (as described below). Other indication systems which will be apparent to the skilled person may provide effective solutions. For example, these might include the use of display panels and/or sound.

In practice, the two filters 170 and 175 may be replaced by crossed polariser screens to prevent stray and unwanted light from outside the apparatus reaching the camera 135. The polarisers would be positioned in a similar fashion to the filters. The nature of the filters or poiarisers depends on the type of illumination used. For example, if the imaging wavelength is near infra-red (NIR) or IR then an IR filter is required to prevent stray IR radiation from entering the apparatus through the front window 140. Alternatively, if the imaging wavelength(s) is that of visible light then crossed polarisers over the front window 140 and the camera 135 could be used. Other similar light blocking or filtering arrangements, which will be apparent to the skilled person, may provide equally effective solutions.

The partially reflecting mirror 145 may comprise a glass screen with a surface coating which reflects IR and NIR optical radiation and transmits visible light. Screens of this type are sometimes known as heat-reflecting filters or "hot-mirrors". An advantage of this type of mirror is that, to some extent at least, the mirror also acts as a filter to IR radiation reaching the eye and to visible light reaching the camera. Other forms of lens, filter, beam splitter and/or prism arrangement could be used.

The overall size of the apparatus depends mainly on the size of the opening for the eye 120 and on the level of comfort and ease of use required by a user of the apparatus. The hardware for the apparatus is designed onto a single application specific integrated circuit (ASIC) chip, the size of which is not a limiting factor to the size of the apparatus.

Also, known CCD cameras can have dimensions on the order of millimetres and are not a limiting factor of the apparatus size.

Although FIG. 1 shows the line-of-sight of the imaging apparatus as being directly through a barrel, it will be appreciated that the line-of-sight may instead be via path bending optics such as mirrors or prisms and may include lenses. Such arrangements may provide for an even more compact design and may enhance the image of the outside environment received by the user or the image of the eye received by the camera.

In FIG. 1, the line of sight is an optical path through the barrel. It is envisaged, however, that the line of sight could be provided by a screened image of the environment beyond the apparatus, for example, on a liquid crystal display (LCD) screen. The image could be provided by a CCD camera mounted on the front of the apparatus. Thus, it would be possible to superimpose graphical indicators onto the image to aid the user in aligning the said apparatus with the remote apparatus. Alternatively, the LCD screen may be substantially transparent, to allow the user to see the actual environment beyond the apparatus, and the screen could be used purely for superimposing alignment, or other, information over the actual image. Correct alignment could be established by monitoring a series of signals being emitted by one of the imaging apparatus or the remote apparatus and being received and processed by the other. Although such an arrangement is technically more complex than a simple line-of-sight arrangement through a barrel, as electronic devices such as CCD cameras and displays become smaller and cheaper, such a technically more complex arrangement might make more practical sense.

FIG. 2 shows one possible hardware architecture arrangement for the apparatus. As already stated, the processing hardware is preferably engineered onto a single ASIC chip. The apparatus is controlled by a processor 200 which runs software held in read-only memory (ROM) 205. The processor 200 is connected via a bus 210 to the ROM 205, a block of random access memory (RAM) 215 and an input/output (I/O) controller 220. The RAM is large enough to hold at least one captured image of an eye. The I/O controller 220 is connected by appropriate circuitry and drivers (not shown) to the IR transmitter 160 and receiver 162, the CCD camera 135, the trigger 165, the IR illumination source 150 and the optical indicator 185. The whole apparatus is powered by a suitable battery (not shown).

The processor 200 is sensitive to signals received from the trigger 165, the IR receiver 162 and the CCD camera 135. Also, the processor controls the IR transmitter 160, the IR illumination source, the CCD camera operation and the optical indicator 185.

Figure 3:
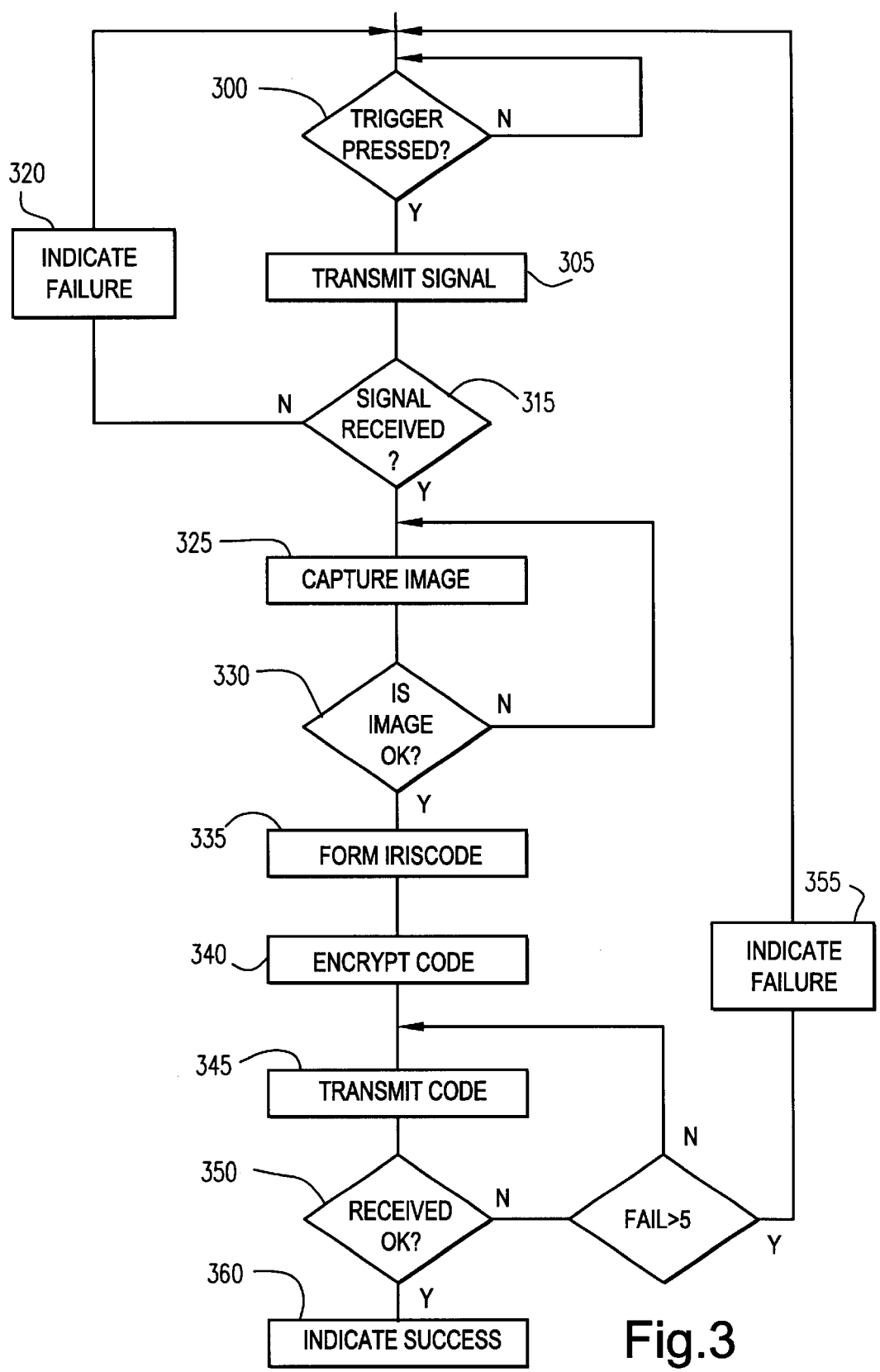
FIG. 3 is a flow chart of an image capturing and encryption process.

The flow diagram in FIG. 3 illustrates one possible process for the image capturing, processing and transmitting aspects of a user validation system. This procedure includes encryption to enhance the level of security. The encryption system uses a 'public key' to encipher data and a private key (known only to the recipient of the enciphered data) to decipher the data.

In step 300, the imaging apparatus is in a state where a trigger depression is awaited to start the process. When the user presses the trigger, the trigger generates a signal which is received by the processor. The processor then controls the IR transmitter to send a signal, in step 305, to the remote apparatus to initiate communications. In response, the remote apparatus sends a return message to the imaging apparatus.

In other embodiments, the trigger is substituted by the imaging apparatus, or the remote apparatus, monitoring for correct alignment. When correct alignment is established by the user, the capture, encoding and transmitting operations are initiated. Monitoring would involve one or other of the apparatuses emitting a signal which could be received and processed by the other apparatus to indicate correct alignment.

If the return message is not received by the imaging apparatus in step 315, for example as a result of the remote apparatus not receiving the first signal, the optical indicator lights up red in step 320 to indicate failure and inform the user to re-start the process by pressing the trigger again.

If the return message is received in step 315, the signal from the remote apparatus includes a selection of which public encryption key and which iris code format the imaging apparatus must use for successful transmission. A plurality of public encryption keys and a plurality of iris code algorithms from which the selection can be made are stored in. the RAM (or the ROM) in the imaging apparatus. The remote apparatus also transmits a date and time stamp to the imaging apparatus.

The information in the return signal, transmitted by the remote apparatus, is stored in the RAM in the imaging apparatus for subsequent access.

Next, in step 325, the processing means signals to the camera that one or more images should be captured. The images which are captured are stored in the RAM. In step 330, the processing means determines if the stored image, or which image, is suitable for encoding. If the, or none of the, images is/are suitable, the processor signals to the camera to re-capture the image(s).

The image capturing step includes control of the illumination source. The illumination source is connected in a control loop whereby the processor can vary the light intensity of the source depending on, for example, the colour of the user's iris: a light blue iris reflects far more light and needs less illumination than a dark brown iris. Several sequentially captured images, similar to a video sequence, might be required for the processor and software to determine the optimum illumination for the eye before a suitable image, or suitable images, is/are obtained.

It is suggested that pulsing the illumination source is more desirable than using a continuous source, although the image capture would need to be synchronised with a pulse of light to ensure suitable illumination. Pulsing light has the advantage that the user's eye is exposed, on average, to less optical radiation. Also, a pulsed source uses less energy.

Capturing multiple images can also overcome problems such as, for example, the user blinking at the point when one image is captured. Known digital signal processing techniques can be used to establish which image is the best and to reject unsuitable images.

When a suitable image is obtained, the image data is retrieved from the RAM and is processed to form an iris code, in step 335, using the iris code generating algorithm selected by the remote apparatus in step 315. An example algorithm is that described in U.S. Pat. No. 5,291,560. The resulting iris code is stored in the RAM.

The processor then encrypts the iris code, in step 340, using the selected public key, along with the date and time stamp provided by the remote apparatus in step 315. The resulting data is stored in RAM. The coded and encrypted data is then transmitted to the remote apparatus by the IR transmitter in step 345.

It is feasible that the image capture, processing and encryption steps are completed without any intervening steps of storing data in RAM, that is to say processing is done "on-the-fly", to greatly increase the speed of operation of the apparatus. However, such processing would require more expensive and more complex electronics.

Finally, if the data is received successfully by the remote apparatus, the remote apparatus returns a 'success' signal to the imaging apparatus in step 350. The processing means, in response, causes the optical indicator to light up green to indicate to the user that the procedure has been successful in step 360. Repeated failure to transmit the data, for example after five attempts, causes the optical indicator to light up red in step 355 and results in the user needing to restart the whole procedure.

A simpler process than that described above involves the imaging apparatus dictating which of the plurality of public encryption keys to use. The selection can be made using a pseudo-random number generator in the imaging apparatus. If each public key has an index reference, the respective reference can be included, obviously in non-encrypted form, with the encrypted data to indicate to the remote apparatus which public key has been used and, thus, which private key should be used for de-encryption. An extension to this arrangement is that a new set of public keys is down-loaded to the imaging apparatus, from the remote apparatus, each time a successful transaction occurs. Other, further encryption possibilities will be apparent to the skilled person.

In alternative embodiments, security may be further improved with the use of a personal identity card similar, for example, to a bank card which holds personal identity information on a magnetic strip. Alternatively, the personal identity card might be a smart-card which holds data in electronic form. The card, smart card, or an equivalent card or device, provides information in the form of magnetic or electronic data held on the card, which identifies a particular user. This information can be read by the imaging apparatus, when the card is inserted into a suitable slot provided therein, and incorporated into the iris code along with, for example, other time stamp and apparatus identity information, further similar embodiments will become apparent to the skilled person.

Figure 4A:
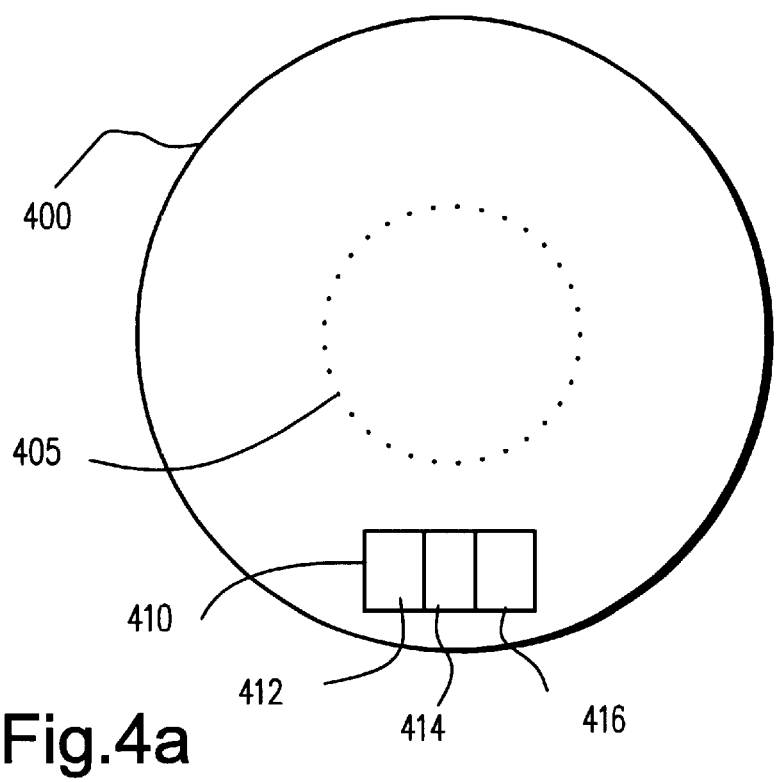
FIGS. 4a and 4b are diagrams which illustrate possible configurations of illumination sources.

FIG. 4a represents one possible configuration for illumination having a plurality of different wavelength sources 412, 414 and 416. The diagram represents the view through the first window 400 to the camera 405 (the diagram does not take account of the 45° mirror). At the bottom of the view area inside the body of the apparatus is provided an light-emitting diode (LED) array comprising three LEDs, each producing NIR optical radiation of a different wavelength band beyond about 700 nm. For example, each band spreads over about 20 nm and each band is separated from the next by about 200 nm. One of the LEDs may instead provide visible light.

One reason for providing illumination sources having different wavelengths stems from the observation that different lighting conditions, to some extent, provide different images. This is a result of the iris of an eye being a three-dimensional object in which different wavelengths of light penetrate to, and reflect from, different depths. For example, IR optical radiation penetrates more deeply into the iris than visible light. Thus, a broadband light source creates a far richer, more complex, image of an iris than a narrow band light source can. An advantage of using a narrow band light source is that a simpler image is produced which can be captured using relatively cheap optics.

The Applicants have determined that different narrow band light sources can be used to produce different iris images which as a group form a family of images for one iris. Thus, one or more of the images can be used to identify or validate a user. The choice of which image to use can be determined by the remote apparatus. This approach increases security by overcoming fraud which might be possible otherwise by substituting a user with a photograph of an eye. Since a photograph is only two-dimensional, there would be no, or at least a different, wavelength dependence in the images produced, and the image would not vary regardless of which wavelength of source was used.

Other embodiments in which separate images resulting from different wavelengths of illumination are combined in different ways will be apparent to the skilled person.

In practice, the array, and each of the LEDs individually, is controlled by the processor (via suitable electrical circuitry which is not shown). The processor controls when and which LEDs light up to illuminate the eye, either in response to its own controlling software or in response to signals received from the remote equipment. The processor also determines when, and under which lighting conditions, the image capturing process occurs. Said lighting conditions depend on the image(s) required by the remote equipment and, as has already been described, may be pulsed.

Figure 4B:
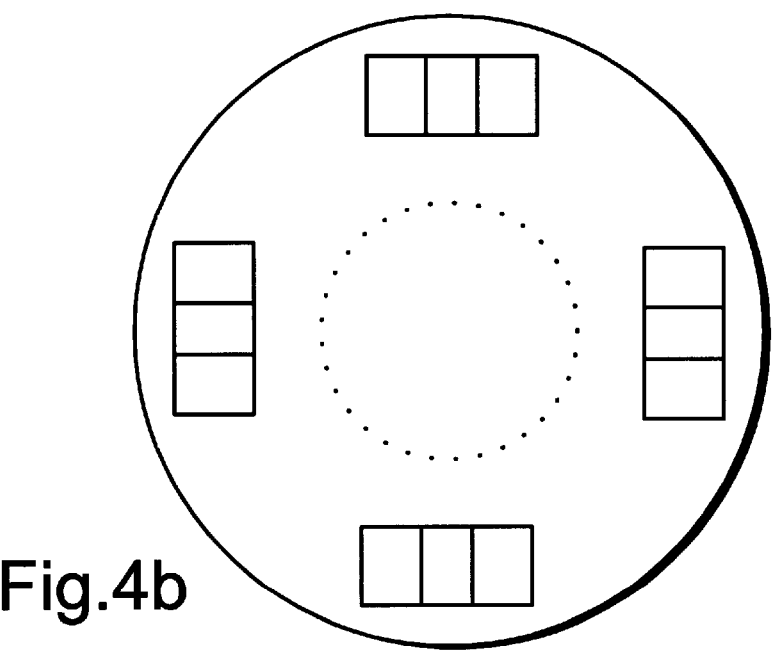

FIG. 4b is similar to FIG. 4a, except four identical LED arrays are provided to produce a more even illumination of the eye.

Instead of different wavelength sources, one or more broadband sources may be used to illuminate the iris, with optical filters used to isolate the required, different wavelength bands.

The procedure relies on the remote apparatus being arranged to receive, transmit and react in a complimentary fashion to the imaging apparatus. In one embodiment, the remote apparatus is a PC programmed with suitable software and having a suitable transmitter and receiver arrangement. Also, the PC is typically connected via a data network to other remote apparatus, for example a database server. In operation, once received by the PC, the encrypted iris code data is directed across the network to the database server. The database server decodes the data and accepts or rejects the user as a valid or an invalid user.

Figure 5A:
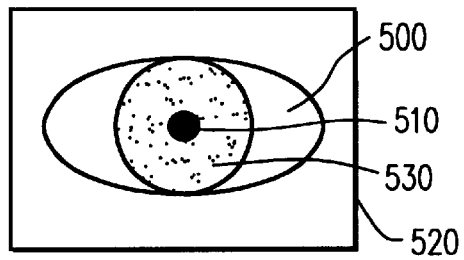
FIGS. 5a and 5b are diagrams which illustrate correct and incorrect eye alignments respectively.

FIG. 5a illustrates correct alignment of an eye 500 with respect the rear window 520 of the apparatus. Correct alignment in this example requires that the whole iris 530 of the eye 500 is in the field of view of the window 520.

Figure 5B:
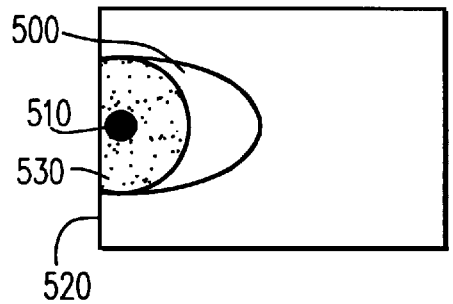

FIG. 5b, which uses the same reference numerals as FIG. 5a, illustrates a potential problem with eye alignment with respect to the rear window 520 of the apparatus. As shown, it is possible that the pupil 510 of the eye 500 has a view through the window 520, but at the same time a significant portion of the iris 530 is obscured from view through the window. Whilst the user might have a reasonable view through the apparatus of, for example, target equipment, the CCD camera 135 would be unable to capture a full iris image, which would prevent successful iris recognition.

Figure 6:
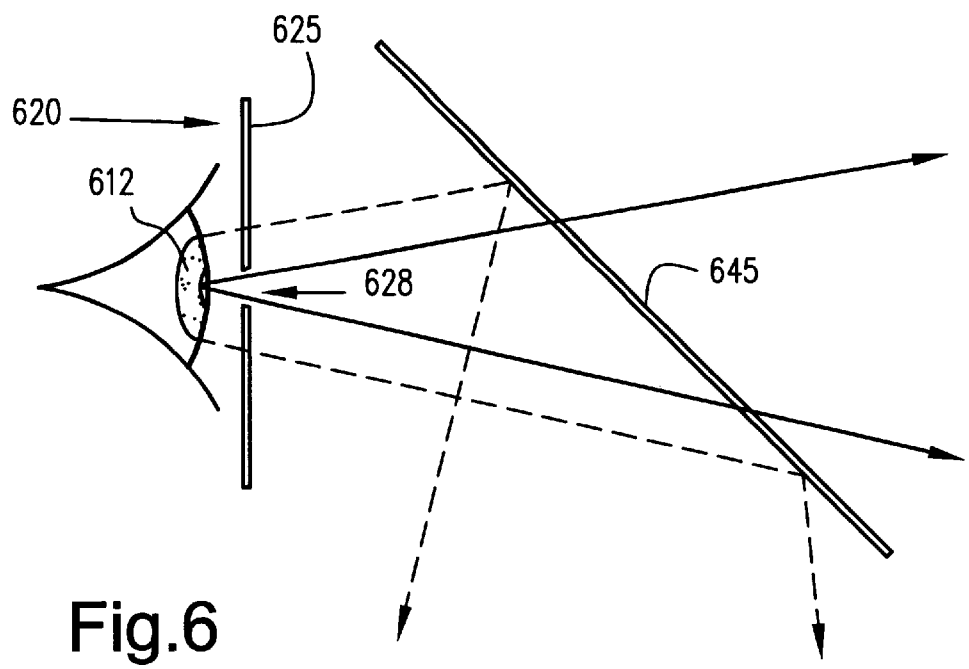
FIG. 6 is a diagram which illustrates an arrangement of apparatus to overcome the incorrect alignment illustrated in FIG. 5b.

FIG. 6 illustrates one possible way of encouraging a user to align their eye correctly in relation to the rear window 620 of the apparatus. The rear window 620 of the apparatus incorporates a screen 625. The screen comprises a gelatin filter, for example a Kodak™ Wratten filter No. 89B, which is transparent to wavelengths greater than 700 nm and opaque to lower, visible wavelengths. The screen has a hole 628 at or around its centre which allows all wavelengths of light to pass through the screen. The hole 628 is large enough to allow the pupil of the eye a view (indicated by solid projection lines) through the screen. This view is not interrupted by a 45° mirror 645 which is substantially transparent to visible wavelengths of optical radiation, but reflecting to IR and NIR wavelengths.

The major portion of the screen 625 is opaque to visible wavelengths of radiation, but transparent to IR and NIR wavelengths. Thus, with suitable IR or NIR illumination (not shown), an image of the iris 612 of the eye, visible through the screen 625 and projected via the mirror 645 to a camera (not shown), can be captured (as illustrated by the dashed projection lines).

Other appropriate compositions of screen will become apparent to the skilled person in view of the preceding description. Indeed, any variations of screen providing a similar advantage could be employed. For example, the major region may be translucent rather than opaque to visible light. Alternatively, the major region may simply be tinted with respect to the minor, pupil aligning region to encourage the user to adopt the correct alignment. Also, the screen may be reinforced with glass or plastics materials, covering the hole to prevent, for example, dust from entering the apparatus.

Clearly, an eye alignment technique employing a screen as described above has potentially broader application than use in conjunction with an apparatus according to the present invention. Indeed, such a screen could be incorporated into any device or apparatus requiring similar, correct eye alignment in relation to the respective apparatus.

As an alternative to the hot mirror used in the above embodiment, a cold-mirror may be used. The cold mirror has the same position and orientation as the hot mirror but has a different coating on its underside. The coating would be effective to reflect most visible light whilst allowing the passage of near infra-red light. The other alteration which is made in this alternative embodiment is to swap the CCD camera and the LCD display about.

Obviously, also, the imaging apparatus according to the invention has far wider application than database access user validation. For example, the apparatus could be used to identify the owner of a car to an engine immobiliser in the car: unless the user is the owner, the car cannot be started. Many other uses of the invention will become apparent to the skilled person on reading the present description.

What is claimed is:

1. An apparatus for providing an information signal characteristic of an eye, said apparatus comprising:
   a housing having an entrance window;
   an image capture device mounted within the housing, in optical communication with said entrance window, and operable to provide an image signal representing one or more features of the eye responsive to non-visible light reflected from the eye;
   an illumination source operable to illuminate the eye with light, at least a portion of which is non-visible;
   a target object visible, in use, through said entrance window by the eye;
   an optical element disposed, in use, across the optical path between said eye and the target object and across the optical path between the image capture device and the eye, said optical element being substantially transparent to said non-visible light, and having a first region which is less transparent to visible light from said target object than a second region thereof; the arrangement being such that, when aligned for use, the image capture device views the eye through said first region and the eye views the target object through the second region.

2. An apparatus according to claim 1 wherein said first region is larger than said second region.

3. An apparatus according to claim 1 wherein said first region surrounds said second region.

4. An apparatus according to claim 3 wherein said second region is positioned substantially at or near the centre of the first region.

5. An apparatus according to claim 1 wherein said first region is substantially opaque to visible light.

6. An apparatus according to claim 1 wherein said non-visible light comprises near intra-red light.

7. Apparatus according to claim 1 wherein said target object comprises a further window, in optical communication with said entrance window to provide said eye with a view beyond the housing.

8. Apparatus according to claim 6 wherein said target object comprises a visual display means which, in use, is visible to the eye.

9. Apparatus according to claim 1 wherein:
   said apparatus is arranged to be carried into an operative position by a user;
   said illumination source is operable to illuminate the surface of the eye over an area outside the pupil;
   said image signal represents one or more features of the anterior of the eye; and
   said apparatus further comprises;
      information signal provision means arranged in operation to derive an information signal from said image signal; and
      a transmission device operable to transmit said information signal derived from said image signal to a remote apparatus.

10. Apparatus according to claim 9 wherein the apparatus is adapted to be held in the hand.

11. Apparatus according to claim 9 wherein said transmission device comprises a cordless transmission means.

12. Apparatus according to claim 1 further comprising means to operate the illumination source in a pulsed manner.

13. An apparatus according to claim 1 further comprising a wavelength selective reflector effective to reflect substantially all of either said visible light or said non-visible light and to allow the passage of substantially all of the other.

14. An apparatus for capturing information characteristic of one or both of a user's eyes, the apparatus comprising:
   a) a housing having a window; and
   b) means for locating one or both of the user's eyes in predetermined relation to the window;
wherein the housing in provided with:
   c) means for illuminating the eye(s) with non-visible illumination;
   d) means for capturing information characteristic of the eye(s) responsive to non-visible light;
   e) means for transmitting the information to remote apparatus; wherein the locating means includes alignment means, the alignment means being provided by the window, a first region of the window being relatively less transparent to visible optical radiation than a second region thereof, and both the first and second regions being transparent to said non-visible light; the arrangement being such that, when aligned for use, the capture device views the eye through said first region and the eye views a target object through the second region, said target object being visible, in use, through said window by the eye.

15. Apparatus according to claim 14 wherein said non-visible light comprises infra-red or near infra-red light.

* * * * *